(12) United States Patent
Parker et al.

(10) Patent No.: US 8,697,906 B2
(45) Date of Patent: Apr. 15, 2014

(54) METHODS AND APPARATUS FOR PRODUCING A LOW-MOISTURE CARBOXYLIC ACID WET CAKE

(75) Inventors: Kenny Randolph Parker, Afton, TN (US); Philip Edward Gibson, Kingsport, TN (US)

(73) Assignee: Grupo Petrotemex, S.A. de C.V., San Pedro Garza Garcia (MX)

( * ) Notice: Subject to any disclaimer, the term of this patent is extended or adjusted under 35 U.S.C. 154(b) by 43 days.

(21) Appl. No.: 11/709,464

(22) Filed: Feb. 22, 2007

(65) Prior Publication Data

US 2007/0208200 A1     Sep. 6, 2007

Related U.S. Application Data

(60) Provisional application No. 60/777,894, filed on Mar. 1, 2006.

(51) Int. Cl.
 *C07C 51/42* (2006.01)
(52) U.S. Cl.
 USPC .................................................... 562/474
(58) Field of Classification Search
 USPC ............... 423/405, 480, 485; 528/114, 189; 562/485, 486
 See application file for complete search history.

(56) References Cited

U.S. PATENT DOCUMENTS

| | | |
|---|---|---|
| 3,152,947 A | 10/1964 | Monick et al. |
| 3,425,135 A | 2/1969 | Langsetmo et al. |
| 3,943,233 A | 3/1976 | Swanson et al. |
| 4,158,738 A | 6/1979 | Scott et al. |
| 4,161,578 A | 7/1979 | Herron |
| 4,219,669 A | 8/1980 | Tsuchiya et al. |
| 4,268,972 A | 5/1981 | Molls et al. |
| 4,330,676 A | 5/1982 | Moxham |
| 4,356,319 A | 10/1982 | Roffia et al. |
| 4,495,070 A | 1/1985 | Pierson |
| 4,589,215 A | 5/1986 | Iwasaki et al. |
| 4,658,891 A | 4/1987 | Wurtz |
| 4,769,489 A | 9/1988 | Abrams et al. |
| 4,792,621 A | 12/1988 | Abrams |
| 4,894,117 A | 1/1990 | Bianchi et al. |
| 4,914,230 A | 4/1990 | Abrams et al. |
| 4,939,297 A | 7/1990 | Browder et al. |
| 5,043,007 A | 8/1991 | Davis |

(Continued)

FOREIGN PATENT DOCUMENTS

| | | |
|---|---|---|
| EP | 0 858 990 A1 | 8/1998 |
| EP | 1 402 942 A1 | 3/2004 |
| GB | 1 470 574 | 4/1977 |

OTHER PUBLICATIONS

Copending U.S. Appl. No. 11/701,128, filed Feb. 1, 2007, Kenny Randolph Parker et al.

(Continued)

*Primary Examiner* — Carlos Barcena
(74) *Attorney, Agent, or Firm* — Oblon, Spivak, McClelland, Maier & Neustadt, L.L.P.

(57) ABSTRACT

Disclosed are methods and apparatus for use in producing a low-moisture carboxylic acid wet cake. Such a low-moisture wet cake can comprise less than about 12 weight percent liquid and can be achieved by washing a carboxylic acid wet cake in a product isolation zone with a wash stream having an initial temperature of at least about 40° C.

42 Claims, 4 Drawing Sheets

(56) References Cited

U.S. PATENT DOCUMENTS

Figure 1:
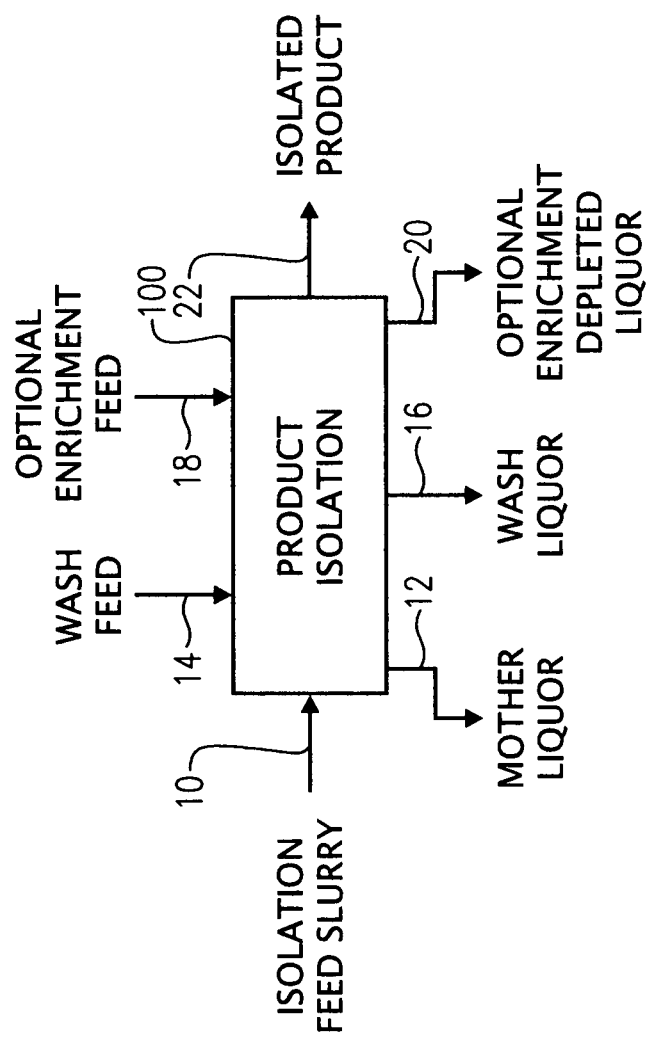

| | | |
|---|---|---|
| 5,100,510 A | 3/1992 | Bianchi et al. |
| 5,175,355 A | 12/1992 | Streich et al. |
| 5,200,557 A * | 4/1993 | Gee et al. ............ 562/486 |
| 5,271,163 A | 12/1993 | Pikus et al. |
| 5,563,293 A | 10/1996 | Hindmarsh et al. |
| 5,583,254 A | 12/1996 | Turner et al. |
| 5,643,468 A | 7/1997 | Ure |
| 5,676,847 A | 10/1997 | Yamamoto et al. |
| 5,698,734 A | 12/1997 | Turner et al. |
| 5,705,682 A | 1/1998 | Ohkoshi et al. |
| 5,767,311 A | 6/1998 | Lee et al. |
| 5,770,765 A | 6/1998 | Ohkoshi |
| 5,840,965 A | 11/1998 | Turner et al. |
| 5,840,968 A | 11/1998 | Lee et al. |
| 5,877,271 A | 3/1999 | Billovits et al. |
| 5,877,346 A | 3/1999 | Hindmarsh et al. |
| 5,973,196 A | 10/1999 | Takano et al. |
| 6,013,835 A | 1/2000 | Lee et al. |
| 6,031,128 A | 2/2000 | Roh et al. |
| 6,054,610 A | 4/2000 | Lee et al. |
| 6,113,866 A | 9/2000 | Lee et al. |
| 6,143,926 A | 11/2000 | Parten |
| 6,150,553 A | 11/2000 | Parten |
| 6,153,790 A | 11/2000 | June et al. |
| 6,245,939 B1 | 6/2001 | Hsu et al. |
| 6,307,099 B1 | 10/2001 | Turner et al. |
| 6,310,239 B1 | 10/2001 | Roh et al. |
| 6,562,997 B2 | 5/2003 | Sikkenga et al. |
| 6,580,005 B1 | 6/2003 | Yazaki et al. |
| 6,620,966 B2 | 9/2003 | Ohkoshi et al. |
| 6,639,104 B2 | 10/2003 | Piras et al. |
| 6,655,531 B1 | 12/2003 | Beard et al. |
| 6,765,113 B2 | 7/2004 | Graham et al. |
| 7,074,954 B2 | 7/2006 | Sheppard et al. |
| 7,132,566 B2 | 11/2006 | Sumner, Jr. et al. |
| 2002/0016500 A1 | 2/2002 | Matsumoto et al. |
| 2002/0193630 A1 | 12/2002 | Lin et al. |
| 2003/0004372 A1 | 1/2003 | Piras et al. |
| 2003/0004373 A1 | 1/2003 | Piras et al. |
| 2003/0059516 A1 | 3/2003 | Brubacher et al. |
| 2004/0098877 A1 | 5/2004 | Stock et al. |
| 2004/0142079 A1 | 7/2004 | Brubacher et al. |
| 2004/0191139 A1 * | 9/2004 | Numata et al. ............ 422/245.1 |
| 2004/0244536 A1 | 12/2004 | Lin |
| 2004/0245176 A1 | 12/2004 | Parker et al. |
| 2004/0249208 A1 | 12/2004 | Lin et al. |
| 2005/0000108 A1 | 1/2005 | Ragnarsson |
| 2005/0159616 A1 | 7/2005 | Parker et al. |
| 2005/0159617 A1 | 7/2005 | Parker et al. |
| 2005/0228164 A1 | 10/2005 | Lin et al. |
| 2006/0047165 A1 | 3/2006 | Lin et al. |

OTHER PUBLICATIONS

Copending U.S. Appl. No. 11/701,129, filed Feb. 1, 2007, Kenny Randolph Parker et al.

Office Action issued Sep. 1, 2011 in Chinese Patent Application No. 200780007419.8 (with English translation).

Office Action issued Mar. 1, 2013 in Chinese Patent Application No. 200780007419.8 with English language translation.

Office Action issued Aug. 15, 2012 in Chinese Patent Application No. 200780007419.8 (with English-language translation).

Article entitled "Case Study—Failure Study of a Petrochemical Rotary Dryer," by Expert Solutions Group, no date available.

Brochure entitled "A Turn for the Better In Thermal Processing," by Bepex Corporation, 1992 Bepex.

Brochure entitled "Thermal Processing—Beyond the Basics," by Bepex International LLC, 2005 Bepex.

Article entitled "Solidaire," by Bepex International LLC, retrieved from the internet at http://www.bepex.com/torusdisc.htm, on Nov. 12, 2009.

Article entitled "Torusdisc—Single or Twin Rotor Dryer," by Bepex International LLC, retrieved from the internet at http://www.bepex.com/torusdisc.htm, on Nov. 12, 2009.

* cited by examiner

METHODS AND APPARATUS FOR PRODUCING A LOW-MOISTURE CARBOXYLIC ACID WET CAKE

RELATED APPLICATIONS

This application claims the priority benefit of U.S. Provisional Pat. App. Ser. No. 60/777,894 filed Mar. 1, 2006, the entire disclosure of which is incorporated herein by reference.

BACKGROUND OF THE INVENTION

1. Field of the Invention

The present invention relates generally to methods and apparatus for minimizing the moisture in a carboxylic acid product wet cake. More specifically, the present invention concerns methods and equipment suitable to produce a carboxylic acid particulate product wet cake comprising less than about 12 weight percent moisture.

2. Description of the Prior Art

In conventional crude terephthalic acid (CTA) production processes, para-xylene undergoes oxidation to form CTA particles. The CTA particles are then typically subjected to isolation and washing. In a conventional purified terephthalic acid (PTA) production process, an additional step is employed where the CTA is purified prior to the isolation/washing step. In either a CTA or a PTA production process, the terephthalic acid (TPA) particles exiting the isolation/washing step are typically in the form of a wet cake. In some TPA production processes, the wet cake is then dried in a dryer to thereby produce a dried TPA product.

Various techniques are known in the art for isolating TPA particles from a slurry. An example of one such technique includes the use of a vacuum filter. Vacuum filters typically employ a filter cloth through which the liquid phase of the slurry is drawn using a vacuum source, thus leaving a filter cake of TPA particles on the cloth. However, conventional techniques for isolating TPA can be problematic due to the fact that product wet cakes produced using these techniques typically have a relatively high moisture content. A TPA product wet cake having a high moisture content will require more extensive drying to be suitable for sale or use in subsequent processes, thus increasing overall production costs. Accordingly, there is a need in the industry for methods and apparatus that are capable of reducing the moisture content of an isolated TPA product wet cake.

SUMMARY OF THE INVENTION

One embodiment of the present invention concerns a method for isolating solid particles comprising an aromatic dicarboxylic acid. The method of this embodiment comprises: treating a slurry comprising a liquid and said solid particles in a product isolation zone to thereby produce a mother liquor and a low-moisture wet cake comprising at least a portion of said solid particles, wherein said treating comprises washing at least a portion of said solid particles with a wash stream having an initial temperature of at least about 40° C., wherein said low-moisture wet cake comprises less than about 12 weight percent liquid.

Another embodiment of the present invention concerns a method for producing a low-moisture wet cake comprising solid particles of terephthalic acid. The method of this embodiment comprises: (a) introducing a slurry comprising said solid particles and a liquid into a product isolation zone; (b) separating said slurry into a mother liquor and an initial wet cake; (c) washing said initial wet cake with a wash feed having an initial temperature of at least about 40° C. to thereby produce a washed wet cake and a wash liquor; and (d) dewatering said washed wet cake with a dewatering gas to produce said low-moisture wet cake, wherein said low-moisture wet cake comprises less than about 12 weight percent liquid.

Yet another embodiment of the present invention concerns a method for minimizing moisture in a wet cake comprising terephthalic acid (TPA). The method of this embodiment comprises: treating a slurry comprising said TPA and a liquid in a catalyst removal zone to thereby produce a mother liquor and said wet cake comprising TPA, wherein said treating comprises washing at least a portion of said TPA with a wash stream having an initial temperature of at least about 40° C., wherein said wet cake comprises less than about 12 weight percent moisture.

BRIEF DESCRIPTION OF THE DRAWING FIGURES

Figure 2:
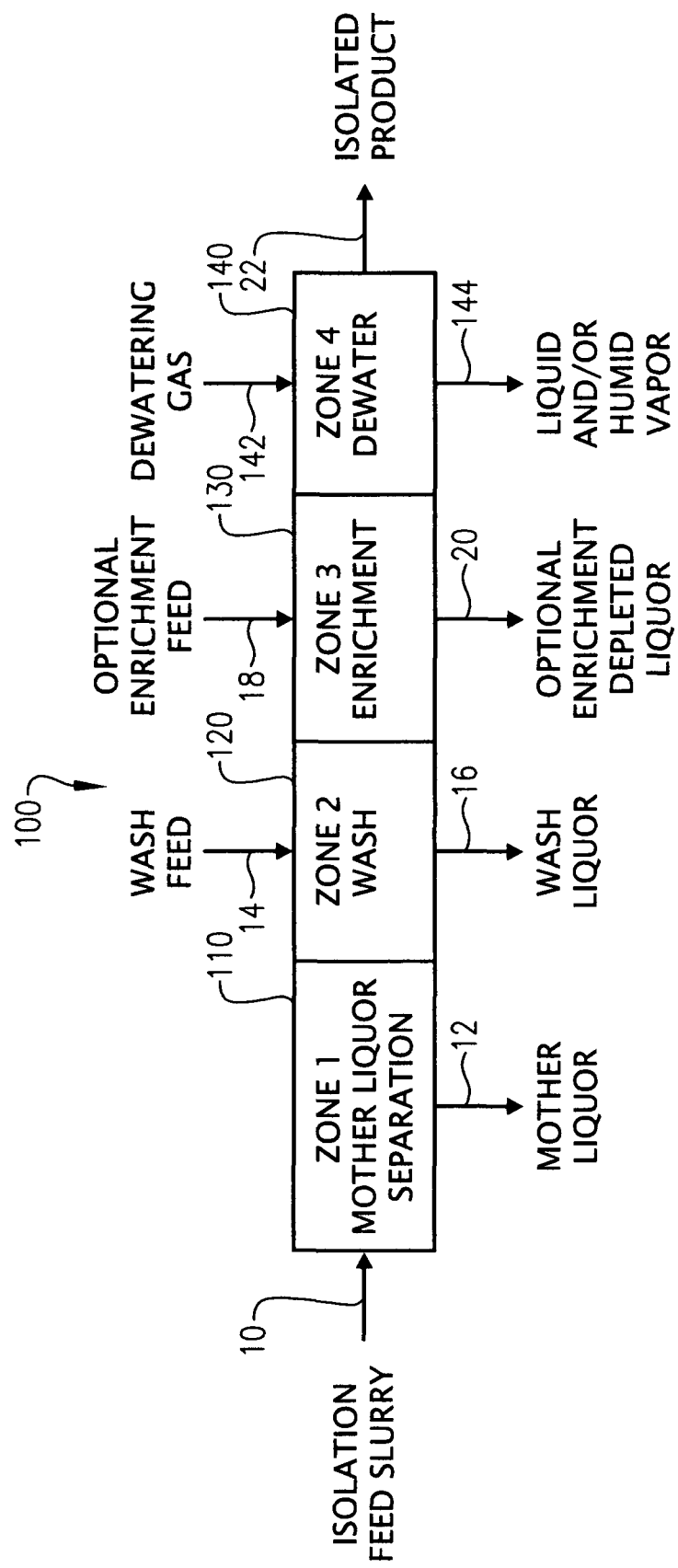
Figure 3:
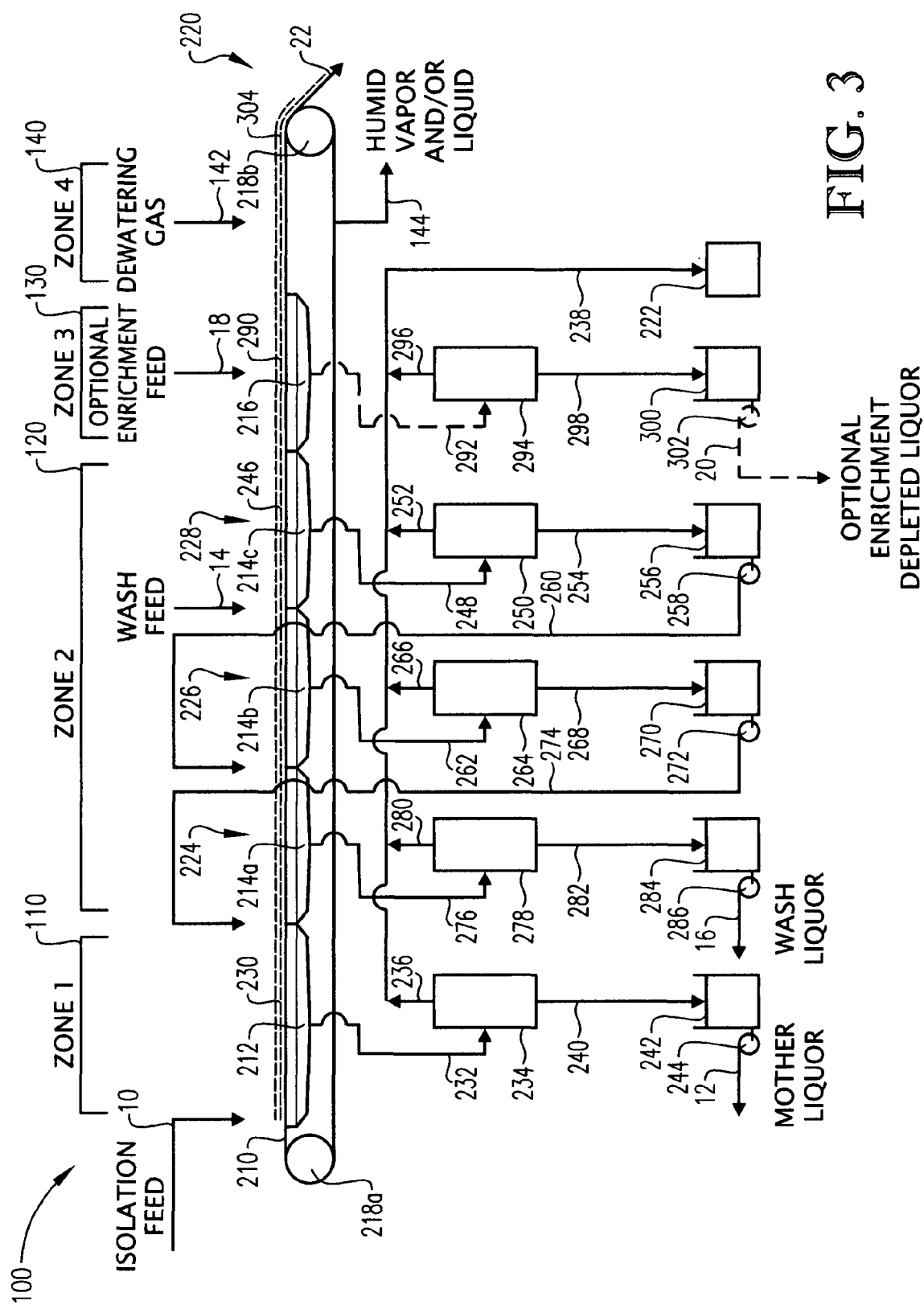
Figure 4:
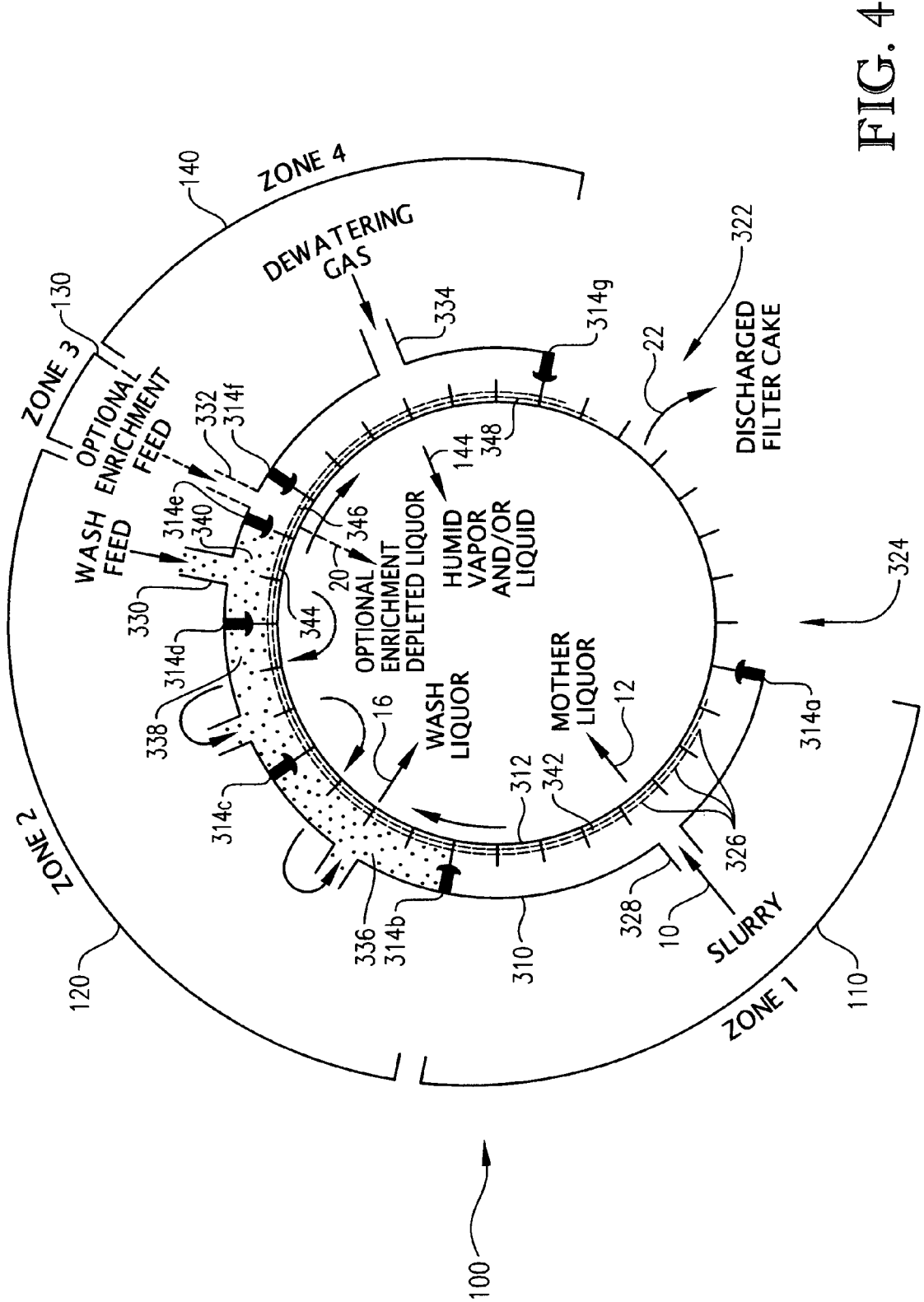

A preferred embodiment of the present invention is described in detail below with reference to the attached drawing figures, wherein:

FIG. 1 is process flow diagram illustrating an overview of a product isolation zone constructed in accordance with the present invention, particularly illustrating a configuration where an isolation feed slurry, a wash feed, and an optional enrichment feed are introduced into the product isolation zone, and a mother liquor, a wash liquor, an optional enrichment depleted liquor, and an isolated product are withdrawn from the product isolation zone;

FIG. 2 is a process flow diagram illustrating a product isolation zone constructed in accordance with the present invention, particularly illustrating a configuration where the product isolation zone comprises a mother liquor separation zone, a wash zone, an optional enrichment zone, and a dewater zone;

FIG. 3 is a schematic representation of a vacuum belt filter that can be employed in the present invention as a product isolation zone to isolate carboxylic acid particles from the liquid phase of a slurry produced by one or more oxidation reactors; and FIG. 4 is a schematic representation of a rotary pressure drum filter that can be employed in the present invention as a product isolation zone to isolate carboxylic acid particles from the liquid phase of a slurry produced by one or more oxidation reactors.

DETAILED DESCRIPTION

FIG. 1 illustrates an embodiment of the present invention where an isolation feed slurry can be treated in a product isolation zone 100. The product isolation zone can separate the isolation feed slurry into a primarily fluid phase mother liquor, a wash liquor, and a primarily solid phase isolated product wet cake comprising isolated solids.

In the embodiment of FIG. 1, an isolation feed slurry can be introduced into product isolation zone 100 via line 10. In one embodiment, product isolation zone 100 can be a catalyst removal zone. The isolation feed slurry can comprise a liquid phase and solid particles. In one embodiment, the isolation feed slurry can comprise solid particles in an amount in the range of from about 1 to about 50 weight percent, in the range of from about 5 to about 40 weight percent, or in the range of from 20 to 35 weight percent. The solid particles in the isolation feed slurry can have a mean particle size of at least about 10 microns, in the range of from about 10 to about 500 microns, in the range of from about 20 to about 400 microns, or in the range of from 30 to 300 microns. Additionally, the solid particles in the isolation feed slurry can comprise a carboxylic acid. In one embodiment, the carboxylic acid can be an aromatic dicarboxylic acid. The solid particles can have an average concentration of carboxylic acid of at least about 50 weight percent, at least about 75 weight percent, or at least 95 weight percent. In one embodiment, the solid particles can be crude particles such as crude terephthalic acid (CTA) particles. In another embodiment, the solid particles can be purified particles such as purified terephthalic acid (PTA) particles. In one embodiment, the solid particles can comprise 4-carboxybenzaldehyde (4-CBA) in an amount of less than about 400 ppmw, less than about 250 ppmw, or in the range of form 10 to 200 ppmw.

The isolation feed slurry in line 10 can comprise the above-mentioned liquid phase in an amount in the range of from about 50 to about 99 weight percent. Additionally, the liquid phase of the isolation feed slurry in line 10 can comprise an aliphatic acid in an amount of at least about 60 weight percent, at least about 75 weight percent, or at least 85 weight percent. The aliphatic acid can comprise an aliphatic carboxylic acid having from 1 to 6 carbon atoms. In one embodiment, the aliphatic acid can comprise acetic acid. Furthermore, the liquid phase of the isolation feed slurry can comprise water.

In one embodiment, the isolation feed slurry in line 10 can have an initial temperature of at least about 40° C., in the range of from about 40 to about 180° C., in the range of from about 50 to about 160° C., or in the range of from 60 to 140° C. As used herein with respect to the isolation feed slurry, the term "initial temperature" is defined as the temperature of the isolation feed slurry immediately upon being introduced into product isolation zone 100.

The isolation feed slurry in line 10 can be a slurry produced in a carboxylic acid production process. An example of such a carboxylic acid production process can comprise introducing a predominately fluid-phase feed stream containing an oxidizable compound (e.g., para-xylene), a solvent (e.g., acetic acid and/or water), and a catalyst system (e.g., cobalt, manganese, and/or bromine) into an oxidation reactor (not shown). A predominately gas-phase oxidant stream containing molecular oxygen can also be introduced into the oxidation reactor. The fluid- and gas-phase feed streams can form a multi-phase reaction medium in the oxidation reactor. The oxidizable compound can undergo at least partial oxidation in a liquid phase of the reaction medium contained in the oxidation reactor.

The oxidizable compound present in the fluid-phase feed stream can comprise at least one hydrocarbyl group. Also, the oxidizable compound can comprise an aromatic compound. In one embodiment, the oxidizable compound can comprise an aromatic compound with at least one attached hydrocarbyl group or at least one attached substituted hydrocarbyl group or at least one attached heteroatom or at least one attached carboxylic acid function (—COOH). In another embodiment, the oxidizable compound can comprise an aromatic compound with at least one attached hydrocarbyl group or at least one attached substituted hydrocarbyl group with each attached group comprising from 1 to 5 carbon atoms. In yet another embodiment, the oxidizable compound can be an aromatic compound having exactly two attached groups with each attached group comprising exactly one carbon atom and consisting of methyl groups and/or substituted methyl groups and/or at most one carboxylic acid group. Suitable examples of the oxidizable compound include, but are not limited to, para-xylene, meta-xylene, para-tolualdehyde, meta-tolualdehyde, para-toluic acid, and/or meta-toluic acid. In one embodiment of the present invention, the oxidizable compound comprises para-xylene.

A "hydrocarbyl group," as defined herein, is at least one carbon atom that is bonded only to hydrogen atoms and/or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. "Aromatic compounds," as defined herein, comprise an aromatic ring and can comprise at least 6 carbon atoms and can also comprise only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the fluid-phase feed stream introduced into the oxidation reactor can be in the range of from about 4 to about 20 weight percent, or in the range of from 6 to 15 weight percent.

The solvent present in the fluid-phase feed stream introduced into the oxidation reactor can comprise an acid component and a water component. The solvent can be present in the fluid-phase feed stream at a concentration in the range of from about 60 to about 98 weight percent, in the range of from about 80 to about 96 weight percent, or in the range of from 85 to 94 weight percent. The acid component of the solvent can be an organic low molecular weight monocarboxylic acid having from 1 to 6 carbon atoms, or 2 carbon atoms. In one embodiment, the acid component of the solvent can comprise acetic acid. The acid component can make up at least about 75 weight percent of the solvent, at least about 80 weight percent of the solvent, or in the range of from 85 to 98 weight percent of the solvent, with the balance being water.

As mentioned above, the fluid-phase feed stream introduced into the oxidation reactor can also include a catalyst system. The catalyst system can be a homogeneous, liquid-phase catalyst system capable of promoting at least partial oxidation of the oxidizable compound. Also, the catalyst system can comprise at least one multivalent transition metal. In one embodiment, the catalyst system can comprise cobalt, bromine, and/or manganese.

When cobalt is present in the catalyst system, the fluid-phase feed stream can comprise cobalt in an amount such that the concentration of cobalt in the liquid phase of the reaction medium is maintained in the range of from about 300 to about 6,000 parts per million by weight (ppmw), in the range of from about 700 to about 4,200 ppmw, or in the range of from 1,200 to 3,000 ppmw. When bromine is present in the catalyst system, the fluid-phase feed stream can comprise bromine in an amount such that the concentration of bromine in the liquid phase of the reaction medium is maintained in the range of from about 300 to about 5,000 ppmw, in the range of from about 600 to about 4,000 ppmw, or in the range of from 900 to 3,000 ppmw. When manganese is present in the catalyst system, the fluid-phase feed stream can comprise manganese in an amount such that the concentration of manganese in the liquid phase of the reaction medium is maintained in the range of from about 20 to about 1,000 ppmw, in the range of from about 40 to about 500 ppmw, or in the range of from 50 to 200 ppmw.

In one embodiment of the present invention, cobalt and bromine can both be present in the catalyst system. The weight ratio of cobalt to bromine (Co:Br) in the catalyst system can be in the range of from about 0.25:1 to about 4:1, in the range of from about 0.5:1 to about 3:1, or in the range of from 0.75:1 to 2:1. In another embodiment, cobalt and manganese can both be present in the catalyst system. The weight ratio of cobalt to manganese (Co:Mn) in the catalyst system can be in the range of from about 0.3:1 to about 40:1, in the range of from about 5:1 to about 30:1, or in the range of from 10:1 to 25:1.

During oxidation, the oxidizable compound (e.g., para-xylene) can be continuously introduced into the oxidation reactor at a rate of at least about 5,000 kilograms per hour, at a rate in the range of from about 10,000 to about 80,000 kilograms per hour, or in the range of from 20,000 to 50,000 kilograms per hour. During oxidation, the ratio of the mass flow rate of the solvent to the mass flow rate of the oxidizable compound entering the oxidation reactor can be maintained in the range of from about 2:1 to about 50:1, in the range of from about 5:1 to about 40:1, or in the range of from 7.5:1 to 25:1.

The predominately gas-phase oxidant stream introduced into the oxidation reactor can comprise in the range of from about 5 to about 40 mole percent molecular oxygen, in the range of from about 15 to about 30 mole percent molecular oxygen, or in the range of from 18 to 24 mole percent molecular oxygen. The balance of the oxidant stream can be comprised primarily of a gas or gases, such as nitrogen, that are inert to oxidation. In one embodiment, the oxidant stream consists essentially of molecular oxygen and nitrogen. In another embodiment, the oxidant stream can be dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in the oxidation reactor, the oxidant stream can be introduced into the oxidation reactor in an amount that provides molecular oxygen somewhat exceeding the stoichiometric oxygen demand. Thus, the ratio of the mass flow rate of the oxidant stream (e.g., air) to the mass flow rate of the oxidizable compound (e.g., para-xylene) entering the oxidation reactor can be maintained in the range of from about 0.5:1 to about 20:1, in the range of from about 1:1 to about 10:1, or in the range of from 2:1 to 6:1.

The liquid-phase oxidation reaction carried out in the oxidation reactor can be a precipitating reaction that generates solids. In one embodiment, the liquid-phase oxidation carried out in the oxidation reactor can cause at least about 10 weight percent of the oxidizable compound (e.g., para-xylene) introduced into the oxidation reactor to form solids (e.g., CTA particles) in the reaction medium. In another embodiment, the liquid-phase oxidation carried out in the oxidation reactor can cause at least about 50 weight percent of the oxidizable compound (e.g., para-xylene) introduced into the oxidation reactor to form solids (e.g., CTA particles) in the reaction medium. In yet another embodiment, the liquid-phase oxidation carried out in the oxidation reactor can cause at least about 90 weight percent of the oxidizable compound (e.g., para-xylene) introduced into the oxidation reactor to form solids (e.g., CTA particles) in the reaction medium. In one embodiment, the solids content of the reaction medium can be maintained in the range of from about 1 to about 50 weight percent, in the range of from about 5 to about 40 weight percent, in the range of from about 10 to about 35 weight percent, or in the range of from 15 to 30 weight percent. As used herein, the term "solids content" shall denote the weight percent solids in a multi-phase mixture.

During oxidation in the oxidation reactor, the multi-phase reaction medium can be maintained at an elevated temperature in the range of from about 125 to about 200° C., in the range of from about 150 to about 180° C., or in the range of from 155 to 165° C. The overhead pressure in the oxidation reactor can be maintained in the range of from about 1 to about 20 bar gauge (barg), in the range of from about 2 to about 12 barg, or in the range of from 4 to 8 barg.

In one embodiment of the present invention, a crude slurry can be withdrawn from an outlet of the oxidation reactor. The solid phase of the crude slurry can be formed primarily of CTA particles. The liquid phase of the crude slurry can be a mother liquor comprising at least a portion of the solvent, one or more catalyst components, and minor amounts of dissolved terephthalic acid (TPA). The solids content of the crude slurry can be the same as the solids content of the reaction medium in the oxidation reactor, discussed above. In one embodiment of the present invention, at least a portion of the crude slurry can be employed as the isolation feed slurry introduced into product isolation zone 100.

In one embodiment of the present invention, the crude slurry can comprise impurities. As used herein, the term "impurities" is defined as any substance other than TPA, solvent, catalyst, and water. Such impurities can include oxidation byproducts formed during the at least partial oxidation of the above-mentioned oxidizable compound (e.g., para-xylene) including, but not limited to, benzoic acid (BA), bromo-benzoic acid, bromo-acetic acid, isophthalic acid, trimellitic acid, 2,5,4'-tricarboxybiphenyl, 2,5,4'-tricarboxybenzophenone, para-toluic acid (p-TAc), 4-carboxybenzaldehyde (4-CBA), monocarboxyfluorenones, and/or dicarboxyfluorenones.

Subsequent to removal from the oxidation reactor, at least a portion of the crude slurry can be purified in a purification zone (not shown). In one embodiment, the crude slurry can be treated in the purification zone such that the concentration of at least one of the above-mentioned impurities in the crude slurry is reduced, thereby producing a purified slurry. Such reduction in the concentration of impurities in the TPA can be accomplished by oxidative digestion, hydrogenation, and/or dissolution/recrystallization.

In one embodiment of the present invention, the crude slurry fed to the purification zone can have a 4-CBA content of at least about 100 parts per million based on the weight of the solids in the crude slurry (ppmw$_{cs}$), in the range of from about 200 to about 10,000 ppmw$_{cs}$, or in the range of from 800 to 5,000 ppmw$_{cs}$. The crude slurry fed to the purification zone can have a p-TAc content of at least about 250 ppmw$_{cs}$, in the range of from about 300 to about 5,000 ppmw$_{cs}$, or in the range of from 400 to 1,500 ppmw$_{cs}$. After treatment of the crude slurry, a purified slurry can be withdrawn from the purification zone. The purified slurry exiting the purification zone can have a 4-CBA content of less than about 150 parts per million based on the weight of the solids in the purified slurry (ppmw$_{ps}$), less than about 100 ppmw$_{ps}$, or less than 50 ppmw$_{ps}$. The purified slurry exiting the purification zone can have a p-TAc content of less than about 300 ppmw$_{ps}$, less than about 200 ppmw$_{ps}$, or less than 150 ppmw$_{ps}$. In one embodiment, treatment of the crude slurry in the purification zone can cause the purified slurry exiting the purification zone to have a 4-CBA and/or p-TAc content that is at least about 50 percent less than the 4-CBA and/or p-TAc content of the crude slurry, at least about 85 percent less, or at least 95 percent less. By way of illustration, if the 4-CBA content of the crude slurry fed to the purification zone is 200 ppmw$_{cs}$ and the 4-CBA content of the purified slurry exiting the purification zone is 100 ppmw$_{ps}$, then the 4-CBA content of the purified slurry is 50 percent less than the 4-CBA content of the crude slurry.

In one embodiment of the present invention, reduction of impurities in the crude slurry can be accomplished by subjecting the crude slurry to oxidative digestion in the purification zone. As used herein, the term "oxidative digestion"

denotes a process step or steps where a feed comprising solid particles is subjected to oxidation under conditions sufficient to permit oxidation of at least a portion of the impurities originally trapped in the solid particles. The purification zone can comprise one or more reactors or zones. In one embodiment, the purification zone can comprise one or more mechanically-agitated reactors. A secondary oxidant stream, which can have the same composition as the gas-phase oxidant stream fed to the oxidation reactor, can be introduced into the purification zone to provide the molecular oxygen required for oxidative digestion. Additional oxidation catalyst can be added if necessary. In an alternative embodiment of the present invention, a stream comprising hydrogen can be introduced into the purification zone for at least partial hydrogenation of the crude slurry.

In one embodiment of the present invention, the above-mentioned purified slurry can be withdrawn from an outlet of the purification zone. The solid phase of the purified slurry can be formed primarily of PTA particles, while the liquid phase can be formed of a mother liquor. The solids content of the purified slurry can be in the range of from about 1 to about 50 weight percent, in the range of from about 5 to about 40 weight percent, or in the range of from 20 to 35 weight percent. The purified slurry can also comprise oxidation byproducts, such as, for example, benzoic acid (BA), bromo-benzoic acid, bromo-acetic acid, isophthalic acid, trimellitic acid, 2,5,4'-tricarboxybiphenyl, 2,5,4'-tricarboxybenzophenone, para-toluic acid (p-TAc), 4-carboxybenzaldehyde (4-CBA), monocarboxyfluorenones, monocarboxyfluorenes, dicarboxyfluorenones and/or dicarboxyfluorenes. In one embodiment of the present invention, at least a portion of the purified slurry can be employed as the isolation feed slurry introduced into product isolation zone 100.

As mentioned above, product isolation zone 100 can separate a mother liquor from the isolation feed slurry. The mother liquor can be withdrawn from product isolation zone 100 via line 12. The mother liquor in line 12 can comprise solvent, one or more catalyst components, oxidation byproducts, and TPA. The solvent in the mother liquor in line 12 can comprise a monocarboxylic acid. In one embodiment, the solvent can comprise water and/or acetic acid. The mother liquor in line 12 can comprise solvent in an amount of at least about 85 weight percent, at least about 95 weight percent, or at least 99 weight percent.

The catalyst components in the mother liquor in line 12 can comprise the catalyst components as described above with reference to the catalyst system introduced into the oxidation reactor (e.g., cobalt, manganese, and/or bromine). The mother liquor in line 12 can have a cumulative concentration of all of the catalyst components in the range of from about 500 to about 20,000 ppmw, in the range of from about 1,000 to about 15,000 ppmw, or in the range of from 1,500 to 10,000 ppmw.

The oxidation byproducts in the mother liquor in line 12 can comprise one or more of the oxidation byproducts discussed above. In one embodiment, the mother liquor in line 12 can have a cumulative concentration of all of the oxidation byproducts in the range of from about 1,000 to about 200,000 ppmw, in the range of from about 2,000 to about 120,000 ppmw, or in the range of from 3,000 to about 60,000 ppmw.

In one embodiment of the present invention, the mother liquor in line 12 can comprise solids in an amount of less than about 5 weight percent, less than about 2 weight percent, or less than about 1 weight percent. Additionally, the mother liquor in line 12 can have a temperature of less than about 240° C., in the range of from about 20 to about 200° C., or in the range of from 50 to 100° C.

In one embodiment of the present invention, a wash feed stream can be introduced into product isolation zone 100 via line 14. The wash feed stream introduced into product isolation zone 100 can operate to wash at least a portion of the solid particles introduced into product isolation zone 100 via the isolation feed slurry. In one embodiment, the wash feed stream in line 14 can have an initial temperature of at least about 40° C., in the range of from about 40 to about 180° C., in the range of from about 50 to about 160° C., or in the range of from 60 to 140° C. In another embodiment, the wash feed stream in line 14 can have an initial temperature of at least about 65° C. As used herein with respect to the wash feed stream, the term "initial temperature" is defined as the temperature of the wash feed stream immediately upon being introduced into product isolation zone 100.

In one embodiment, the wash feed stream in line 14 can comprise an aliphatic acid and/or water. The aliphatic acid in the wash feed stream in line 14 can comprise an aliphatic carboxylic acid having from 1 to 6 carbon atoms. In one embodiment, the aliphatic acid can comprise acetic acid. Any ratio of aliphatic acid to water may be employed in the wash feed stream in line 14, including up to 100 percent aliphatic acid or 100 percent water.

In one embodiment, the weight ratio of the wash feed introduced into product isolation zone 100 to solids from the isolation feed slurry can be at least about 0.2:1, in the range of from about 0.2:1 to about 5:1, in the range of from about 0.3:1 to about 3:1, or in the range of from 0.4:1 to 2:1. After washing at least a portion of the solid particles from the isolation feed slurry, a used wash liquor can be withdrawn from product isolation zone 100 via line 16.

In one embodiment of the present invention, an enrichment feed stream may optionally be introduced into product isolation zone 100 via line 18 to enrich at least a portion of the solid particles from the isolation feed slurry. After enriching at least a portion of the solid particles, an optional enrichment depleted liquor can be withdrawn from product isolation zone 100 via line 20. The enrichment feed stream in line 18 and the enrichment depleted liquor in line 20 can be have compositions substantially the same as the enrichment feeds and enrichment depleted liquors described in U.S. Pat. App. Nos. 2006-0264666 A1 and 2006-0264663 A1, the entire disclosures of which are incorporated herein by reference. In one embodiment, the enrichment feed stream in line 18 can have an initial temperature in the range of from about 20 to about 200° C., in the range of from about 40 to about 160° C., or in the range of from 60 to 120° C. In another embodiment, the enrichment feed stream in line 18 can have an initial temperature of at least about 40° C. As used herein with respect to the enrichment feed stream, the term "initial temperature" is defined as the temperature of the enrichment feed stream immediately upon being introduced into product isolation zone 100.

In one embodiment of the present invention, an isolated product can be withdrawn from product isolation zone 100 via line 22. The isolated product discharged via line 22 can comprise at least about 10 weight percent of the above-mentioned carboxylic acid. Furthermore, the isolated product in line 22 can comprise the above-mentioned solid particles from the isolation feed slurry (e.g., CTA particles or PTA particles) in an amount of at least about 85 weight percent, at least about 88 weight percent, at least about 91 weight percent, at least about 94 weight percent, or at least 97 weight percent. Furthermore, the isolated product can comprise oxidation byproducts, such as those discussed above.

In one embodiment, the isolated product in line 22 can be a low-moisture wet cake. As used herein, the term "low-moisture wet cake" is defined as a wet cake comprising a liquid in an amount of less than about 15 weight percent. In another embodiment, the low-moisture wet cake can comprise less than about 12, less than about 9, less than about 6, or less than 3 weight percent liquid. In still another embodiment, the low-moisture wet cake can comprise moisture in an amount in the range of from about 1 to about 12 weight percent, in the range of from about 1.5 to about 9 weight percent, or in the range of from 2 to 6 weight percent. In one embodiment, the low-moisture wet cake can be a washed wet cake and/or an optionally enriched wet cake.

FIG. 2 illustrates an embodiment of the present invention where product isolation zone 100 comprises a first zone that is a mother liquor separation zone 110, a second zone that is a wash zone 120, a third zone that is an optional enrichment zone 130, and a fourth zone that is a dewater zone 140. In the embodiment of FIG. 2, the isolation feed slurry as discussed above can initially be introduced into mother liquor separation zone 110 via line 10. In mother liquor separation zone 110, at least a portion of the liquid phase of the isolation feed slurry can be removed, thereby generating a mother liquor and an initial wet cake.

The mother liquor generated in mother liquor separation zone 110 can be discharged via line 12, and can have the same composition as the mother liquor discussed above with reference to FIG. 1. The initial wet cake generated by mother liquor separation zone 110 can comprise at least a portion of the solid particles from the isolation feed slurry in line 10. In one embodiment, the initial wet cake can comprise liquid in the range of from about 5 to about 30 weight percent, in the range of from about 10 to about 25 weight percent, or in the range of from 12 to 23 weight percent. Additionally, the initial wet cake can have a thickness in the range of from about 0.25 to about 8 inches. The thickness of the initial wet cake can vary depending on the equipment employed in product isolation zone 100, as will be discussed in further detail below with reference to FIGS. 3 and 4.

At least a portion of the initial wet cake generated in mother liquor separation zone 110 can be introduced into wash zone 120. The initial wet cake in wash zone 120 can be washed with the wash stream introduced into wash zone 120 via line 14, as discussed above with reference to FIG. 1, thus generating a wash liquor and a washed wet cake.

As will be discussed in greater detail below with reference to FIGS. 3 and 4, wash zone 120 can comprise three discreet zones: an initial wash zone, an intermediate wash zone, and a final wash zone. In one embodiment, the wash feed stream in line 14 can first be introduced into the final wash zone to wash at least a portion of the initial wet cake, thereby generating a washed wet cake and a first wash liquor. At least a portion of the first wash liquor can then be introduced into the intermediate wash zone to wash at least a portion of the initial wet cake and generate a second wash liquor. At least a portion of the second wash liquor can then be introduced into the initial wash zone to wash at least a portion of the initial wet cake, thereby generating a final wash liquor. In one embodiment, at least a portion of the final wash liquor can be the wash liquor discharged from product isolation zone 100 via line 16, as mentioned above with reference to FIG. 1.

Referring still to FIG. 2, in one embodiment, the flow of the wash stream in wash zone 120 can be substantially counter current to the movement of the initial wet cake in the wash zone. When the wash flow is counter current to the movement of the initial wet cake, the initial wet cake can first be washed by the above-mentioned second wash liquor, then be washed by the above-mentioned first wash liquor, and finally be washed by the wash feed stream as it is introduced into wash zone 120 via line 14.

In one embodiment of the present invention, the solid particles contained in the initial wet cake can have an average residence time of less than about 2 minutes in wash zone 120. Additionally, the solid particles contained in the initial wet cake can have an average residence time in the range of from about 5 seconds to about 2 minutes in wash zone 120, in the range of from about 10 seconds to about 1.5 minutes, or in the range of from 15 seconds to 1 minute. However, as will be discussed in greater detail below with reference to FIGS. 3 and 4, the residence time of the solid particles in wash zone 120 may vary depending on the equipment employed in product isolation zone 100.

At least a portion of the above-mentioned washed wet cake can be introduced into optional enrichment zone 130. Optional enrichment zone 130 can operate to receive an enrichment feed, thereby enriching the washed wet cake in substantially the same manner as described in U.S. Pat. App. Nos. 2006-0264666 A1 and 2006-0264663 A1, referenced above. In one embodiment, the solid particles contained in the washed wet cake can have an average residence time of less than about 2 minutes, less than about 1.5 minutes, or less than 1 minute in enrichment zone 130. However, as will be discussed in greater detail below with reference to FIGS. 3 and 4, the residence time of the solid particles in enrichment zone 130 may vary depending on the equipment employed in product isolation zone 100. After sufficient enrichment, a washed and optionally enriched wet cake can be discharged from enrichment zone 130.

In one embodiment, at least a portion of the washed and optionally enriched wet cake can be introduced into dewater zone 140. Dewater zone 140 can operate to remove at least a portion of the liquid from the washed and optionally enriched wet cake, thereby producing the above-mentioned isolated product (e.g., a low-moisture wet cake). In one embodiment, a dewatering gas can be introduced into dewater zone 140 via line 142 to facilitate liquid removal from the washed and optionally enriched wet cake. The dewatering gas introduced into dewater zone 140 can have an initial temperature of at least about 20° C., or in the range of from 20 to 200° C. As used herein with respect to the dewatering gas, the term "initial temperature" is defined as the temperature of the dewatering gas immediately upon being introduced into product isolation zone 100. The dewatering gas introduced into dewater zone 140 can be any gas capable of removing at least a portion of the liquid from the washed and optionally enriched wet cake. In one embodiment, the dewatering gas introduced into dewater zone 140 can comprise, for example, nitrogen, carbon dioxide, and/or process off-gases. As used herein, the term "process off-gas" is defined as a gas which was used in the oxidation step of a carboxylic acid production process. Liquid removed from the washed and optionally enriched wet cake can exit dewater zone 140 via line 144, and can exit in a liquid phase and/or a vapor phase. Additionally, the dewatering gas stream passed through the washed and optionally enriched wet cake can exit dewater zone 140 as a humid vapor via line 144. After sufficient dewatering, the isolated product can exit dewater zone 140 via line 22. The isolated product in line 22 can be substantially the same as discussed above with reference to FIG. 1.

In one embodiment of the present invention, product isolation zone 100 can be defined within a vacuum belt filter, similar to the device depicted in FIG. 3. As used herein, the term "vacuum belt filter" denotes a device that uses a pressure differential created by a vacuum source across a conveyor belt filter to facilitate solid/liquid separation.

The vacuum belt filter depicted in FIG. 3 comprises a conveyor belt filter 210, a mother liquor vacuum box 212, wash liquor vacuum boxes 214a, b, c, and an enrichment vacuum box 216. Mother liquor separation zone 110 can be defined by the horizontal length of mother liquor vacuum box 212. Wash zone 120 can be defined by the combined horizontal lengths of wash liquor vacuum boxes 214a, b, and c. Optional enrichment zone 130 can be defined by the horizontal length of enrichment vacuum box 216. Dewater zone 140 can be defined between enrichment vacuum box 216 and roller 218b. A discharge zone 220 can be provided following dewater zone 140.

Referring still to FIG. 3, conveyor belt filter 210 can comprise a filter media such as, for example, a filter cloth. Fluid flow through the filter media can be caused by creating a pressure differential across the filter media. In one embodiment, the pressure differential across the filter media can be created at least in part by common vacuum source 222. Fluid flow through the filter cloth can be discharged into vacuum boxes 212, 214a, b, c, and 216.

The vacuum belt filter depicted in FIG. 3 can comprise a slurry line 10 that can communicate with mother liquor separation zone 110, a wash feed line 14 that can communicate with wash zone 120, an optional enrichment feed line 18 that can communicate with optional enrichment zone 130, and a dewatering gas line 142 that can communicate with dewater zone 140. Wash zone 120 can be divided into an initial wash zone 224, an intermediate wash zone 226, and a final wash zone 228. Initial wash zone 224 can be defined by the horizontal length of wash liquor vacuum box 214a, intermediate wash zone 226 can be defined by the horizontal length of wash liquor vacuum box 214b, and final wash zone 228 can be defined by the horizontal length of wash liquor vacuum box 214c.

In operation, the isolation feed slurry can enter mother liquor separation zone 110 via line 10. The isolation feed slurry in line 10 can be substantially the same as discussed above with reference to FIG. 1. The isolation feed slurry introduced into mother liquor separation zone 110 can form an initial wet cake 230 on the filter media on conveyor belt filter 210. In mother liquor separation zone 110, the mother liquor can be discharged downward into mother liquor vacuum box 212. The mother liquor collected in mother liquor vacuum box 212 can be routed to mother liquor receiver 234 via line 232. Mother liquor receiver 234 can communicate with common vacuum source 222 via line 238 to create reduced pressure conditions in mother liquor receiver 234, which in turn can at least partially create the above-mentioned pressure differential across conveyor belt filter 210. Mother liquor receiver 234 can contain therein a vapor phase and the mother liquor. At least a portion of the vapor phase in mother liquor receiver 234 can be removed via line 236 and can be routed to common vacuum source 222 via line 238. In one embodiment of the present invention, a moisture trap (not shown) can be disposed on line 238 prior to common vacuum source 222. The moisture trap can operate to remove any liquid in line 238 so as to prevent liquid from entering common vacuum source 222. The mother liquor in mother liquor receiver 234 can be discharged via line 240 and can be routed to mother liquor seal tank 242. Mother liquor can be withdrawn from mother liquor seal tank 242 via vacuum pump 244 and can be discharged via line 12. The mother liquor in line 12 can be substantially the same as discussed above with reference to FIG. 1.

Upon obtaining a desired height of initial wet cake 230 in mother liquor separation zone 110, rollers 218a and 218b can rotate to advance conveyor belt filter 210 so that initial wet cake 230 can enter wash zone 120. In the embodiment of FIG. 3, initial wet cake 230 can have a thickness in the range of from about 0.25 to about 5 inches, in the range of from about 0.5 to about 4 inches, or in the range of from 1 to 3 inches.

In wash zone 120, initial wet cake 230 can be washed with a wash feed entering final wash zone 228 via wash feed line 14 to thereby form a washed wet cake 246. The wash feed entering wash zone 120 can be substantially the same as the wash feed discussed above with reference to the wash feed in line 14 of FIG. 1. A first wash liquor can be discharged downward through the filter media of conveyor belt filter 210 into wash liquor vacuum box 214c. The first wash liquor collected in wash liquor vacuum box 214c can be routed to first wash liquor receiver 250 via line 248. First wash liquor receiver 250 can communicate with common vacuum source 222 via line 238 to create reduced pressure conditions in first wash liquor receiver 250, which in turn can at least partially create the above-mentioned pressure differential across conveyor belt filter 210. First wash liquor receiver 250 can contain therein a vapor phase and the first wash liquor. At least a portion of the vapor phase in first wash liquor receiver 250 can be removed via line 252 and can be routed to common vacuum source 222 via line 238. The first wash liquor in first wash liquor receiver 250 can be discharged via line 254 and can be routed to first wash liquor seal tank 256. At least a portion of the first wash liquor can be withdrawn from first wash liquor seal tank 256 via vacuum pump 258 and can be discharged via line 260.

In one embodiment, at least a portion of the first wash liquor in line 260 can be transferred to intermediate wash zone 226 to thereby wash at least a portion of initial wet cake 230. Subsequently, a second wash liquor can be discharged downward through the filter media of conveyor belt filter 210 into wash liquor vacuum box 214b. The second wash liquor collected in wash liquor vacuum box 214b can be routed to second wash liquor receiver 264 via line 262. Second wash liquor receiver 264 can communicate with common vacuum source 222 via line 238 to create reduced pressure conditions in second wash liquor receiver 264, which in turn can at least partially create the above-mentioned pressure differential across conveyor belt filter 210. Second wash liquor receiver 264 can contain therein a vapor phase and the second wash liquor. At least a portion of the vapor phase in second wash liquor receiver 264 can be removed via line 266 and can be routed to common vacuum source 222 via line 238. The second wash liquor in second wash liquor receiver 264 can be discharged via line 268 and can be routed to second wash liquor seal tank 270. At least a portion of the second wash liquor can be withdrawn from second wash liquor seal tank 270 via vacuum pump 272 and can be discharged via line 274.

In one embodiment, at least a portion of the second wash liquor in line 274 can be transferred to initial wash zone 224 to thereby wash at least a portion of initial wet cake 230. Subsequently, a final wash liquor can be discharged downward through the filter media of conveyor belt filter 210 into wash liquor vacuum box 214a. The final wash liquor collected in wash liquor vacuum box 214a can be routed to final wash liquor receiver 278 via line 276. Final wash liquor receiver 278 can communicate with common vacuum source 222 via line 238 to create reduced pressure conditions in final wash liquor receiver 278, which in turn can at least partially create the above-mentioned pressure differential across conveyor belt filter 210. Final wash liquor receiver 278 can contain therein a vapor phase and the final wash liquor. At least a portion of the vapor phase in final wash liquor receiver 278 can be removed via line 280 and can be routed to common vacuum source 222 via line 238. The final wash liquor in final wash liquor receiver 278 can be discharged via line 282 and can be routed to final wash liquor seal tank 284. At least a portion of the final wash liquor can be withdrawn from final wash liquor seal tank 284 via vacuum pump 286 and can be discharged via line 16. The wash liquor in line 16 can be substantially the same as discussed above with reference to FIG. 1.

In the embodiment of FIG. 3, the solid particles from the isolation feed stream can have an average residence time of less than about 2 minutes, less than about 1.5 minutes, or less than 1 minute in wash zone 120. After suitable washing in wash zone 120, rollers 218a and 218b can rotate to advance conveyor belt filter 210 so that washed wet cake 246 can enter optional enrichment zone 130.

In optional enrichment zone 130, washed wet cake 246 can optionally be enriched with an enrichment feed entering optional enrichment zone 130 via enrichment feed line 18 to thereby form a washed and optionally enriched wet cake 290. The enrichment feed entering optional enrichment zone 130 can be substantially the same as the enrichment feed discussed above with reference to the enrichment feed in line 18 of FIG. 1. An optional enrichment depleted liquor can be discharged downward through the filter media of conveyor belt filter 210 into enrichment vacuum box 216. The optional enrichment depleted liquor collected in enrichment vacuum box 216 can be routed to optional enrichment depleted liquor receiver 294 via line 292. Optional enrichment depleted liquor receiver 294 can communicate with common vacuum source 222 via line 238 to create reduced pressure conditions in optional enrichment depleted liquor receiver 294, which in turn can at least partially create the above-mentioned pressure differential across conveyor belt filter 210. Optional enrichment depleted liquor receiver 294 can contain therein a vapor phase and the optional enrichment depleted liquor. At least a portion of the vapor phase in optional enrichment depleted liquor receiver 294 can be removed via line 296 and can be routed to common vacuum source 222 via line 238. The optional enrichment depleted liquor in optional enrichment depleted liquor receiver 294 can be discharged via line 298 and can be routed to optional enrichment depleted liquor seal tank 300. At least a portion of the optional enrichment depleted liquor can be withdrawn from optional enrichment depleted liquor seal tank 300 via vacuum pump 302 and can be discharged via line 20. The optional enrichment depleted liquor can be discharged from product isolation zone 100 via line 20, as discussed above with reference to FIG. 1.

In one embodiment, the solid particles from the isolation feed slurry can have an average residence time of less than about 2 minutes, less than about 1.5 minutes, or less than 1 minute in optional enrichment zone 130. After suitable enriching in optional enrichment zone 130, rollers 218a and 218b can rotate to advance conveyor belt filter 210 so that washed and optionally enriched wet cake 290 can enter dewater zone 140.

In dewater zone 140, liquid can be removed from washed and optionally enriched wet cake 290 by passing a dewatering gas, entering via line 142, through washed and optionally enriched wet cake 290, thereby producing a final wet cake (i.e., an isolated product) 304. The dewatering gas introduced via line 142 can be substantially the same as the dewatering gas discussed above with reference to FIG. 2. Liquid and/or humid vapor can be removed from product isolation zone 100 via line 144, as discussed above with reference to FIG. 2. In the embodiment of FIG. 4, the solid particles from the isolation feed slurry can have an average residence time of less than about 2 minutes, or less than 1.5 minutes in dewater zone 140. After suitable dewatering in dewater zone 140, rollers 218a and 218b can rotate to advance conveyor belt filter 210 so that final wet cake 304 can enter discharge zone 220.

In discharge zone 220, at least a portion of final wet cake 304 can be disengaged from conveyor belt filter 210 and can exit product isolation zone 100 via line 22. In one embodiment, the final wet cake discharged from discharge zone 220 can be substantially the same as the isolated product in line 22, discussed above with reference to FIG. 1.

It will be understood by one skilled in the art that many different configurations of vacuum belt filters are possible, any of which may be used in the present invention. Suitable examples of commercially available vacuum belt filters include, but are not limited to, a PANNEVIS RT horizontal vacuum belt filter, available from LAROX Corp., Lappeenranta, Finland; and a BHS-BELT FILTER, available from BHS-Sonthofen GmbH, D-87527, Sonthofen, Germany.

In one embodiment of the present invention, product isolation zone 100 can be defined within a rotary pressure drum filter, similar to the device depicted in FIG. 4. As used herein, the term "rotary pressure drum filter" denotes a device that uses a pressure differential across a rotating drum filter to facilitate solid/liquid separation. The rotary pressure drum filter depicted in FIG. 4 comprises a housing 310 and a rotary drum filter 312 rotatably disposed within housing 310. An annulus is defined between the inside of housing 310 and the outside of rotary drum filter 312. This annulus is divided into various discreet zones by seals 314a, b, c, d, e, f, g. Mother liquor separation zone 110 can be defined in the annulus between seals 314a and 314b. Wash zone 120 can be defined in the annulus between seals 314b and 314e. Optional enrichment zone 130 can be defined in the annulus between seals 314e and 314f. Dewater zone 140 can be defined in the annulus between seals 314f and 314g. Housing 310 can be open between seals 314g and 314a. This open portion of housing 310 can include a discharge zone 322 and a cloth wash zone 324.

Referring still to FIG. 4, rotary drum filter 312 can define a plurality of filter cells 326 located on the periphery of the drum. The bottom of each filter cell 326 can be formed of a filter media (e.g., synthetic cloth, single-layer metal, or multi-layer metal). Fluid flow through the filter media can be caused by creating a pressure differential across the filter media. Each filter cell 326 has its own outlet for discharging fluids inwardly towards the axis of rotation of rotary drum filter 312. The outlets of axially-aligned filter cells 326 can be manifolded. The manifolds (not shown) can rotate with the rotary drum filter 312 and can communicate with a service/control head (not shown) which can collect the fluids from the manifolds in a manner that allows the fluids discharged from zones 110, 120, 130, and 140 to be kept separate.

Housing 310 can define an isolation feed slurry inlet 328 that can communicate with mother liquor separation zone 110, a wash feed inlet 330 that can communicate with wash zone 120, an optional enrichment feed inlet 332 that can communicate with optional enrichment zone 130, and a dewatering gas inlet 334 that can communicate with dewater zone 140. Wash zone 120 can be divided into an initial wash zone 336, an intermediate wash zone 338, and a final wash zone 340 by seals 314c and 314d. Housing 310 and rotary drum filter 312 can be configured to permit filtrate discharged from final wash zone 340 to enter intermediate wash zone 338, and filtrate discharged from intermediate wash zone 338 to enter initial wash zone 336.

In operation, the isolation feed slurry in line 10 can enter mother liquor separation zone 110 via slurry inlet 328. The isolation feed slurry in line 10 can be substantially the same as discussed above with reference to FIG. 1. The isolation feed slurry introduced into mother liquor separation zone 110 can form an initial wet cake 342 in filter cells 326 on the periphery of rotary filter drum 312. In mother liquor separation zone 110, the mother liquor can be discharged radially inward from the bottom of each filter cell 326. The mother liquor collected from mother liquor separation zone 110 can be discharged from the apparatus via line 12. The mother liquor in line 12 can be substantially the same as discussed above with reference to FIG. 1. Upon obtaining a desired height of initial wet cake 342 in mother liquor separation zone 110, rotary drum filter 312 can rotate so that initial wet cake 342 enters wash zone 120. In the embodiment of FIG. 4, initial wet cake 342 can have a thickness in the range of from about 2 to about 8 inches, in the range of from about 3 to about 7 inches, or in the range of from 4 to 6 inches.

In wash zone 120, initial wet cake 342 can be washed with a wash feed entering final wash zone 340 via wash feed inlet 330 to thereby form a washed wet cake 344. The wash feed entering wash feed inlet 330 can be substantially the same as the wash feed discussed above with reference to the wash feed in line 14 of FIG. 1. The first wash liquor from final wash zone 340 can then be transferred to intermediate wash zone 338, and the second wash liquor from intermediate wash zone 338 can then be transferred to initial wash zone 336. The final wash liquor from initial wash zone 336 can then be discharged from product isolation zone 100 via line 16, as discussed above with reference to FIG. 1. In one embodiment of the present invention, the final wash liquor in line 16 can be combined into the mother liquor in line 12.

In the embodiment of FIG. 4, the solid particles from the isolation feed stream can have an average residence time of less than about 1 minute, less than about 40 seconds, or less than 25 seconds in wash zone 120. After suitable washing in wash zone 120, rotary drum filter 312 can rotate so that washed wet cake 344 can enter optional enrichment zone 130.

In optional enrichment zone 130, washed wet cake 344 can be optionally be enriched with an enrichment feed stream entering optional enrichment zone 130 via enrichment feed inlet 332 to thereby form a washed and optionally enriched wet cake 346. The enrichment feed stream entering enrichment feed inlet 332 can be substantially the same as the enrichment feed stream discussed above with reference to the enrichment feed stream in line 18 of FIG. 1. After enrichment, an optional enrichment depleted liquor can be discharged from product isolation zone 100 via line 20, as discussed above with reference to FIG. 1. In the embodiment of FIG. 4, the solid particles from the isolation feed slurry can have an average residence time of less than about 1 minute, less than about 40 seconds, or less than 25 seconds in optional enrichment zone 130. After suitable enriching in optional enrichment zone 130, rotary drum filter 312 can rotate so that washed and optionally enriched wet cake 346 can enter dewater zone 140.

In dewater zone 140, liquid can be removed from washed and optionally enriched wet cake 346 by passing a dewatering gas, entering via gas inlet 334, through washed and optionally enriched wet cake 346, thereby producing a final wet cake (i.e., an isolated product) 348. The dewatering gas introduced into inlet 334 can be substantially the same as the dewatering gas discussed above with reference to the dewatering gas in line 142 of FIG. 2. Liquid and/or humid vapor can be removed from product isolation zone 100 via line 144, as discussed above with reference to FIG. 2. In the embodiment of FIG. 4, the solid particles from the isolation feed slurry can have an average residence time of less than about 1 minute, or less than 45 seconds in dewater zone 140. After suitable dewatering in dewater zone 140, rotary drum filter 12 can rotate so that final wet cake 348 can enter discharge zone 322.

In discharge zone 322, at least a portion of final wet cake 348 can be disengaged from rotary drum filter 312 and can exit product isolation zone 100 via line 22. Rotary drum filter 312 can then rotate into cloth wash zone 324, where any solid particles remaining in filter cells 326 can be removed. In one embodiment, the final wet cake discharged via discharge zone 322 can be substantially the same as the isolated product in line 22, discussed above with reference to FIG. 1.

It will be understood by one skilled in the art that many different configurations of rotary pressure drum filters are possible, any of which may be used in the present invention. An example of a suitable commercially available rotary pressure drum filter which can be employed in product isolation zone 100 includes, but is not limited to, a BHS-FEST ROTARY PRESSURE FILTER, available from BHS-Sonthofen GmbH, D-87527, Sonthofen, Germany.

It will be understood by one skilled in the art that each of the above-described embodiments, as well as any sub-parts of those embodiments, may be operated in a continuous or a non-continuous manner. Non-continuous operations include, but are not limited to, batch-wise operations, cyclical operations, and/or intermittent operations. Additionally, it will be understood that two or more of the above embodiments may be used in combination.

EXAMPLES

The following examples are intended to be illustrative of the present invention in order to teach one of ordinary skill in the art to make and use the invention and are not intended to limit the scope of the invention in any way.

Example 1

PTA Slurry

A purified terephthalic acid (PTA) slurry was withdrawn from a production process for use in the following example. The PTA slurry was a commercial grade PTA slurry comprising approximately 31 weight percent solid particles of PTA. Additionally, the slurry comprised approximately 62 weight percent acetic acid and approximately 7 weight percent water.

Example 2

Product Wet Cake Moisture Content 12 samples of the PTA slurry described in Example 1 were introduced into a bench scale Pannevis vacuum filter apparatus, available from Pannevis, Inc., Rockaway, N.J., U.S. Each of the 12 samples was then separated into a wet cake and a mother liquor, and the moisture content of each of the wet cakes was measured. The wash temperature and wash ratio were varied according to Table 1 below to determine their effect on moisture content of the isolated product wet cake. In Table 1, the wash ratio is a ratio of the wash mass versus the mass of the solid particles contained in the PTA slurry. For example, a ratio of 0.5 indicates a 0.5:1 ratio of wash mass-to-mass of solid particles. A mono-filament PEEK filter cloth having a pore size of 43 microns was employed for each of the filtrations performed.

TABLE 1

Wet Cake Moisture Content

| Sample No. | Slurry Temp. (° C.) | Wash Temp. (° C.) | Wash Ratio | Slurry Mass (g) | Wash Mass (g) | Wet Cake Percent Moisture |
|---|---|---|---|---|---|---|
| 1 | 65 | 40 | 0 | 484 | 0 | 11 |
| 2 | 65 | 40 | 0.5 | 530 | 79.7 | 10.8 |
| 3 | 65 | 40 | 0.5 | 503 | 76.2 | 10.7 |
| 4 | 65 | 40 | 0.5 | 517 | 77.5 | 13.8 |
| 5 | 65 | 40 | 1 | 520 | 156 | 11.2 |
| 6 | 65 | 15 | 0.5 | 496.6 | 74.7 | 12.1 |
| 7 | 65 | 15 | 1 | 507 | 151.9 | 9.9 |
| 8 | 65 | 65 | 0.5 | 518 | 78 | 10.9 |
| 9 | 65 | 65 | 1 | 497.5 | 152 | 7.6 |
| 10 | 65 | 90 | 0.5 | 501 | 75.5 | 5.3 |
| 11 | 65 | 90 | 1 | 528 | 158.1 | 5.1 |
| 12 | 65 | 90 | 1 | 500 | 150.4 | 2.2 |

As can be seen by looking at the results listed in Table 1, the temperature of the wash stream and the ratio of wash feed to solid particles can have an effect on the percent moisture in the isolated product.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds).

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.+/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively.

Definitions

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Claims Not Limited to Disclosed Embodiments

The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A method for isolating solid particles:
   the solid particles comprising an aromatic dicarboxylic acid,
   said method comprising:
   treating a slurry comprising a liquid and said solid particles in a product isolation zone to thereby produce a mother liquor at a temperature of from 50° C. to 100° C. and a low-moisture wet cake comprising at least a portion of the solid particles,
   wherein the liquid consists essentially of acetic acid or mixtures of acetic acid and water, and
   the slurry treatment comprises washing at least a portion of the solid particles in an initial wet cake formed by removal of the mother liquor with a wash stream consisting essentially of acetic acid or mixtures of acetic acid and water having an initial temperature in a range from 60° C. to 140° C., to provide the low-moisture wet cake having a liquid content of less than 9 weight percent liquid.

2. The method of claim 1, wherein the liquid content of the washed wet cake is less than about 6 weight percent liquid.

3. The method of claim 1, wherein the liquid content of the washed wet cake is less than about 3 weight percent liquid.

4. The method of claim 1, wherein a weight ratio of the wash stream to the solid particles is in a range of from about 0.2:1 to about 5:1.

5. The method of claim 4, wherein the weight ratio of the wash stream to the solid particles is in the range of from about 0.3:1 to about 3:1.

6. The method of claim 1, wherein a thickness of the initial wet cake is in a range of from about 0.25 to about 8 inches.

7. The method of claim 1, wherein the treatment further comprises contacting at least a portion of the washed wet cake with an enrichment feed to thereby produce a washed and enriched wet cake.

8. The method of claim 7, wherein an initial temperature of the enrichment feed is in a range of from about 20° C. to about 200° C.

9. The method of claim 1, wherein the treatment further comprises contacting at least a portion of the washed wet cake with a dewatering gas, wherein an initial temperature of the dewatering gas is at least about 20° C.

10. The method of claim 1, wherein the product isolation zone comprises a mother liquor removal zone, a wash zone, an optional enrichment zone, and a dewatering zone.

11. The method of claim 10, wherein the wash zone comprises an initial wash zone, an intermediate wash zone, and a final wash zone.

12. The method of claim 11, wherein the washing comprises counter current washing.

13. The method of claim 12, wherein the counter current washing comprises introducing the wash feed into the final wash zone thereby producing a first wash liquor, introducing at least a portion of the first wash liquor into the intermediate wash zone thereby producing a second wash liquor, and introducing at least a portion of the second wash liquor into the initial wash zone.

14. The method of claim 10, wherein an average residence time of initial wet cake in the wash zone is less than about 2 minutes.

15. The method of claim 14, wherein the average residence time in the wash zone is in a range of from about 5 seconds to about 2 minutes.

16. The method of claim 10, wherein an average residence time of the washed wet cake in the dewatering zone is less than about 2 minutes.

17. The method of claim 1, wherein the product isolation zone is defined within a rotary pressure drum filter.

18. The method of claim 1, wherein the product isolation zone is defined within a vacuum belt filter.

19. The method of claim 1, wherein the solid particles comprise crude terephthalic acid.

20. The method of claim 1, wherein the solid particles comprise purified terephthalic acid.

21. A method for producing a low-moisture wet cake comprising solid particles of terephthalic acid, the method comprising:
(a) introducing a slurry comprising the solid particles and a liquid consisting essentially of acetic acid or mixtures of acetic acid and water into a product isolation zone;
(b) separating the slurry into a mother liquor at a temperature ranging from 50° C. to 100° C. and an initial wet cake comprising at least a portion of the solid particles;
(c) washing the initial wet cake with a wash feed consisting essentially of acetic acid or mixtures of acetic acid and water, the wash feed having an initial temperature in a range from 60° C. to 140° C., to thereby produce a washed wet cake and a wash liquor; and
(d) dewatering the washed wet cake with a dewatering gas to produce the low-moisture wet cake, wherein a liquid content of the low-moisture wet cake is less than 9 weight percent liquid.

22. The method of claim 21, wherein an initial temperature of the wash feed is in a range of from about 50° C. to about 160° C.

23. The method of claim 21, wherein the liquid content of the low-moisture wet cake is less than 6 weight percent liquid.

24. The method of claim 21, wherein the liquid content of the low-moisture wet cake is less than 3 weight percent liquid.

25. The method of claim 21, wherein a weight ratio of the wash stream to the solid particles is in a range of from about 0.2:1 to about 5:1.

26. The method of claim 25, wherein the weight ratio of the wash stream to the solid particles is in the range of from about 0.3:1 to about 3:1.

27. The method of claim 21, wherein a thickness of the initial wet cake is in a range of from about 0.25 to about 8 inches.

28. The method of claim 21, wherein an initial temperature of the dewatering gas is at least about 20° C.

29. The method of claim 21, wherein the washing (c) is substantially performed within a wash zone, wherein the washing comprises counter current washing.

30. The method of claim 29, wherein an average residence time of the initial wet cake in the wash zone is less than about 2 minutes.

31. The method of claim 21, further comprising after the washing (c), contacting the washed wet cake with an enrichment feed to thereby produce an enriched wet cake, wherein an initial temperature of the enrichment feed is in a range of from about 20° C. to about 200° C.

32. The method of claim 31, wherein the contacting with the enrichment feed is substantially performed within an enrichment zone, and an average residence time of the washed wet cake in the enrichment zone is less than about 2 minutes.

33. A method for minimizing moisture in a wet cake comprising terephthalic acid (TPA), the method comprising: treating a slurry comprising the TPA and a liquid consisting essentially of acetic acid or mixtures of acetic acid and water in a catalyst removal zone to thereby produce a mother liquor comprising a catalyst at a temperature ranging from 50° C. to 100° C. and the wet cake comprising TPA, wherein the treating comprises washing at least a portion of the TPA with a wash stream consisting essentially of acetic acid or mixtures of acetic acid and water wherein an initial temperature of the wash stream is in a range from 60° C. to 140° C., to provide a TPA wet cake having a moisture content of less than 9 weight percent moisture and a reduced catalyst content in comparison to the TPA of the slurry treated.

34. The method of claim 33, wherein an initial temperature of the wash stream is at least about 65° C.

35. The method of claim 33, wherein the moisture content of the TPA wet cake is less than about 6 weight percent moisture.

36. The method of claim 33, wherein the washing comprises counter current washing.

37. The method of claim 33, wherein the catalyst removal zone comprises a mother liquor separation zone, a wash zone, an optional enrichment zone, and a dewatering zone.

38. The method of claim 33, further comprising after washing the TPA cake contacting at least a portion of the TPA cake with an enrichment feed stream to thereby produce an enriched wet TPA cake.

39. The method of claim 38, wherein an initial temperature of the enrichment feed is at least about 40° C.

40. The method of claim 33, further comprising contacting at least a portion of the TPA wet cake with a dewatering gas.

41. The method of claim 33, wherein the catalyst removal zone is defined within a vacuum belt filter.

42. The method of claim 33, wherein the catalyst removal zone is defined within a rotary pressure drum filter.

* * * * *